United States Patent [19]

Ronnett et al.

[11] Patent Number: 5,196,315
[45] Date of Patent: Mar. 23, 1993

[54] HUMAN NEURONAL CELL LINE

[75] Inventors: Gabriele V. Ronnett, Baltimore, Md.; Jeffrey S. Nye, New York, N.Y.; Lynda D. Hester, Towson; Solomon H. Snyder, Baltimore, both of Md.

[73] Assignee: The Johns Hopkins University, Baltimore, Md.

[21] Appl. No.: 689,002

[22] Filed: Apr. 25, 1991

Related U.S. Application Data

[63] Continuation-in-part of Ser. No. 515,760, May 1, 1990, abandoned.

[51] Int. Cl.$^5$ .................. C12Q 1/02; C12N 5/00
[52] U.S. Cl. ................... 435/29; 435/240.2; 435/240.21
[58] Field of Search ............. 435/240.2, 240.21, 29

[56] References Cited

PUBLICATIONS

Ronnet et al, Science vol. 248, May 4, 1990, pp. 603–605.
Hirsch. Brain Research vol. 161 (1979) pp. 277–291.
Nye, et al., Neuroscience Abstracts, 14:92, 1988.
Guggino, et a., Neuroscience Abstracts, 15:996, 1989.
Dr. Lewis L. Judd, Statement for Public Health Service, 1990.
Dr. Frederick Goodwin, Statement for Public Health Serice.
Michael Specter, Washington Post, "Scientists Grow Brain Tissue in Laboratory", May 4, 1990, p. 1.
Borisy, et al., Society for Neuroscience Abstracts, 15:750, 1989.
Abstract of U.S. Ser. No. 07/487,894, filed Jun. 3, 1990.

*Primary Examiner*—Douglas W. Robinson
*Assistant Examiner*—Jane A. Williams
*Attorney, Agent, or Firm*—Banner, Birch, McKie & Beckett

[57] ABSTRACT

This invention is directed to continuous, non-maligant, neuronal cell lines, the cells of which: a) in the undifferentiated form are essentially free of branched process; b) stain positively for neurofilament protein and neurotransmitters; c) do not stain positively for glial fibrillary acidic protein; and d) in the presence of nerve growth factor differentiate into cells with long branched processes. Derivative cell lines of such cell lines are also contemplated. The cell lines are useful in screening methods for evaluation of chemical and biological compounds as well as for therapeutic uses.

6 Claims, 4 Drawing Sheets

HUMAN NEURONAL CELL LINE

This invention was made with government support under contract nos. MH-18501, DA-00266, and DA-00074 awarded by the National Institutes of Health. The government has certain rights in this invention.

This application is a continuation-in-part of Ser. No. 07/515,760 filed May 1, 1990 now abandoned.

BACKGROUND OF THE INVENTION

The failure of neurons in the central nervous system to regenerate is responsible for much of the disability associated with clinical damage to the central nervous system (CNS). Additionally, because CNS neurons do not regenerate, it has not been possible to develop continuous human cultures of such neurons.

The great heterogeneity of the central nervous system (CNS) has precluded extensive molecular characterization of CNS neurons. Techniques previously utilized to establish cell lines have significant limitations. Primary cultures are heterogeneous and have limited life-spans, whereas cell lines derived from malignant tumors and somatic cell hybrids may differ from the mature neuronal phenotype.

Many of the major advances in biomedical research stem from the use of continuous culture of cells from many parts of the body. There is a need for continuous human cortical neuronal cell lines to permit characterization of CNS neurons. Such a continuous cell line would also permit the screening of compounds to determine their effect on neural cells.

SUMMARY OF THE INVENTION

It is an object of this invention to provide continuous, human, neuronal cell lines, which can grow and replicate in vitro.

This invention provides continuous, non-malignant, neuronal cell lines, the cells of which: a) in the undifferentiated form are essentially free of branched processes; b) stain positively for neurofilament protein and neurotransmitters; c) do not stain positively for glial fibrillary acidic protein; and d) in the presence of nerve growth factor differentiate into cells with long branched processes, as well as derivative cell lines thereof.

The continuous cell lines of this invention can be carried for numerous in vitro passages. The cells are important to permit the study of biochemical, physiological, and pharmacological factors that regulate the function of human CNS neurons. The cells are also important for transplantation therapy of diseases of the central nervous system.

DETAILED DESCRIPTION OF THE INVENTION

Figure 1A:
FIG. 1A and 1B. Morphology of undifferentiated HCN-1A cells, which appear polygonal with only occasional short processes (B). Magnification x400.

The human neuronal cell lines of the invention can be maintained and grown in in vitro culture indefinitely even though they are non-malignant. Moreover, and importantly, the cell lines differentiate when nerve growth factor is included in the medium. The cells stain positively for neurofilament protein and for neuron-specific enolase, a marker for neurons. The cells also stain positively for neurotransmitters.

The cells are clonal. Continuous passage for over six months does not significantly alter cellular morphology or growth characteristics. Mature neuronal morphology can be obtained by growing the cells in the presence of a growth factor such as, but not limited to, nerve growth factor, dibutyryl cAMP, and 1-isobutyl-3-methyl xanthine. Other growth factors which increase the intracellular level of cAMP are usable and are known in the art. The differentiated cells display cell bodies with long and branched processes, essentially the same as human cerebral neurons. The cells stain positively for neurofilament protein, which occurs exclusively in neurons. The cells do not stain for glial fibrillary acidic protein. The cells stain positively for neurotransmitters that are characteristic of neurons. The cells are not as primitive as cells in many CNS tumors that have been used for tissue culture.

One cell line of the present invention, HCN-1A, was derived from the continuous culture of cerebral cortex neurons from brain tissue of a patient with unilateral megalencephaly, a low-grade proliferation and migration disorder of neurons. In this condition, there is continued proliferation of immature neuronal cells (M. A. Michael and A. G. Matter, J. Comput. Assisted Tomogr. 2, 291 (1978); M. Dambska, K. Wisniewski, J. H. Sher, Brain Deve. 6,60 (1984)).

Another cell line of the invention, known as HCN-2, was obtained from cells of a seven year-old girl who had undergone hemispherectomy for intractable epilepsy associated with Rasmussen's encephalitis. This second patient has provided cells in continuous culture whose properties are essentially the same as those of HCN-1A cells. The cells of the cell line contain the same neuronal markers as HCN-1A cells. Isolation of a Cell Line Cerebral cortical tissue was obtained form an 18-month-old female undergoing hemispherectomy for intractable seizures (A. R. Goodman, Dev. Med. Child Neurol. 28, 251 (1986). Cortical tissue was grossly dissected into gray and white matter, and the gray matter was immediately placed in minimal essential medium containing D-valine (MDV) (Gibco, Grand Island, N.Y.) and 15% dialyzed fetal bovine serum (dFBS) (Gibco), prepared by dialysis in tubing with a 12,000 to 14,000-dalton cut-off. Tissue was then finely minced and pushed through a 150-um mesh wire screen. This cell suspension was distributed among twelve 35-mm culture wells at a density of approximately 1×10⁴ cells per square centimeter and placed in a 7% $CO_2$ humidified incubator at 37° C. The cell lines were maintained in MDV containing 15% dFBS and passaged by trypsinization [0.05% (w/v) in Hanks' balanced salt solution (Gibco)].

After 21 days all cells had died except for two small foci of growth, which were cloned and designated HCN-1 and HCN-4. These cells were passaged more than 20 times in the course of 19 months with no significant changes in morphology or growth characteristics. Although both of these cell lines originated from small foci of growth in culture, to ensure clonality they were subcloned. One of these attempts yielded a subclone from HCN-1 cells, designated HCN-1A. Both the parental and subcloned line have identical growth, morphologic and staining characteristics.

The HCN-1A cell line has been deposited on Apr. 27, 1990, under the provisions of the Budapest Treaty at the American Type Culture Collection, Rockville, Md. as cell line CRL 10442.

Figure 1B:

For light microscopy, HCN-1A cells were quickly rinsed three times with phosphate-buffered saline (PBS) at 37° C., fixed for 15 min with 4% (w/v) paraformaldehyde, and mounted with PBS. The cells appear epithelioid (FIG. 1, A and B) and rarely extend short processes (FIG. 1B).

Cells grew to confluence but were contact-inhibited beyond this density. Doubling time was approximately 72 hours. Karyotype analysis demonstrated a chromosomal number of 46+2 (R. I. Freshney, Culture of Animal Cells: A Manual of Basic Technique, Liss, N.Y., 1987, pp. 175–176).

a. Effect of Agents on Growth and Morphology

The influence of various agents on the growth and morphology of HCN-1A cells was examined. Nerve growth factor (NGF), insulin, dexamethasone, the phorbol ester 12-0 tetradecanoyl phorbol-13—acetate (TPA), ascorbic acid, dibutyryl cAMP, 1-isobutyl-3-methyl xanthine (IBMX), and retinoic acid were examined alone and in various combinations. The most mature morphology, with considerably slowed growth (a doubling time of 120 hours) occurred in cells grown with a mixture of IBMX, NGF, and dibutyryl cAMP.

Figure 2A:
FIG. 2A and 2B. Morphology of differentiated HCN-1A cells. Whereas undifferentiated cells were flat and polygonal, differentiated cells demonstrated multipolar (A) or bipolar (B) morphologies. All cells had spines and varicosities along their processes.
Figure 2B:
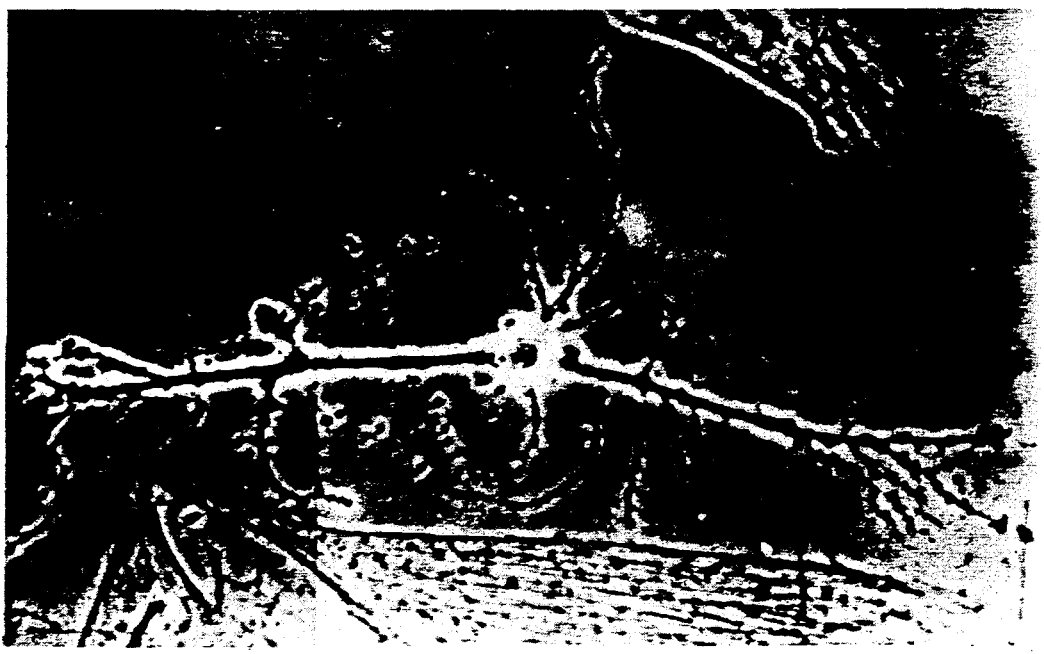

For differentiation, HCN-1A cells at 50% confluence were treated with medium containing 0.5 mM IBMX, 0.5 mM dibutyryl CAMP, and NGF (Collaborative Research, Cambridge, Mass.). Cells were fed every 3 days in this manner and fixed in 4% paraformaldehyde at day 5. The undifferentiated HCN-1A cells were generally flat and polygonal with occasional short, unbranched processes. By contrast, the differentiated cells displayed round cell bodies with numerous, long and extensively branched processes with spines and varicosities. The differentiated cells were either bipolar or multipolar (FIG. 2). One hundred percent of cells differentiated over a 3-day period Withdrawal of the differentiating agents caused retraction of processes, but cellular division remained slow with a doubling time of more than 120 hours.

b. Presence of Neural Proteins

Figure 3A:
FIG. 3A, 3B, 3C and 3D. Immunocytochemical staining of differentiated HCN-1A cells. (FIG. A and FIG. b) Cells stain positively for neurofilament protein (NF) with three different monoclonal antibodies. The results of staining with two these (from Labsystems and Sternberger-Meyer) are shown (FIG. C and FIG. D).
Figure 3B:
Figure 3C:
Figure 3D:
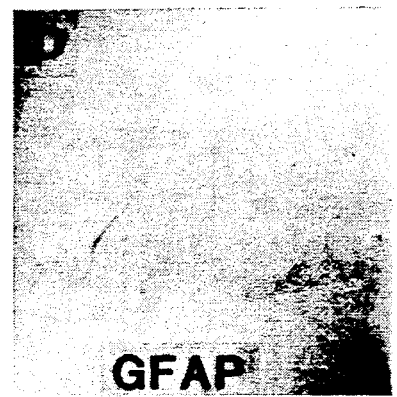
Figure 4A:
FIG. 4A, 4B, 4C, 4D and 4E. Immunocytochemical staining of differentiated HCN-1A cells for neurotransmitters (S-M. Hsu L. Raine. M. Fargen. J. Histochem. Cytochem. 29, 577 (1981)). HCN-1A cells were grown, fixed and stained as described: HCN-1A cells stain positively with antibodies (Incstar) against (FIG. A) GABA at 1:500 dilution, (FIG. B) SST at 1:500 dilution, (FIG. C) VIP at 1:500 dilution, (FIG. D) CCK-8 at 1:500 dilution, and (FIG. E) glutamate (GLU) at 1:250 dilution; nonimmune serum (NI) was negative (FIG. 4F).
Figure 4B:
Figure 4C:
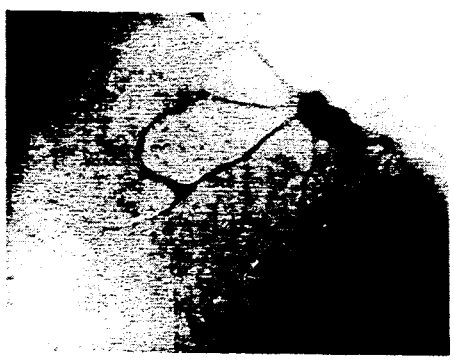
Figure 4D:
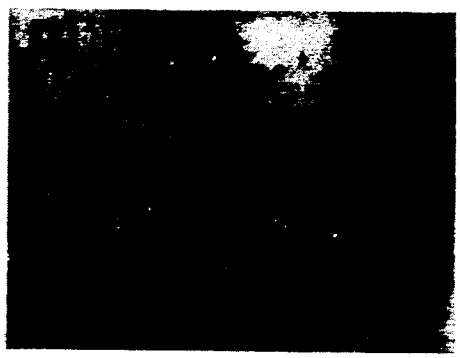
Figure 4E:
Figure 4F:
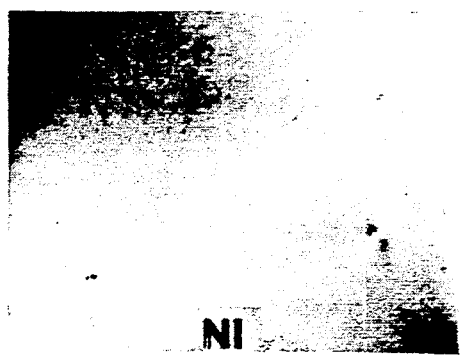

To further characterize the cells, they were stained with antibodies to neurofilament protein (which occurs in neurons), neuron-specific enolase (NSE), glial fibillary acidic protein (GFAP) (which occurs exclusively in astrocytes), vimentin, myelin basic protein (MBP) (which occurs exclusively in oligodendrocytes), S-100, and tubulin. HCN-1A cells were quickly rinsed three times with PBS at 37° C., permeabilized with 0.1% Triton X-100 for 15 min. fixed with 4% paraformaldehyde for 15 min. and rinsed three times with PBS. Immunocytochemical staining was performed with Vector (Burlingame, Calif.) ABC kits; the chromogen used was 3-amino-9-ethyl carbazole, (Biomdea, Foster City, Calif.). Primary antisera used were monoclonal antibody to rat neurofilament (Labsystems, Helsinki, Finland at 1:75 dilution (Fig. 3A), monoclonal antibody to rat neurofilament antibody SMI 33 (Sternberger-Meyer, Jarrettsville, Md.) at 1:2000 dilution (FIG. 3B); rabbit antibody to GFAP (DAKO-Patts, Santa Barbara, Calif.) at 1:800 dilution (FIG. 3D). There was negligible nonspecific staining where immune primary serum was deleted or replaced by nonimmune serum. In addition, specificity of staining for each antibody was checked with rat brain control slides and by protein immunoblotting. Cells were fixed for immunohistochemistry when they were about 50% differentiated because, if all cells are allowed to differentiate, they tend to lift off the slides during fixation.

As with the undifferentiated HCN-1A cells, 100% of the differentiated HCN-1A cells stained positively for neurofilament protein. They also all stained positively for NSE but were negative got GFAP. Additionally, the cells were positive for vimentin and tubulin. Undifferentiated and differentiated cells were negative for S-100 and MBP, both of which occur in glia.

To confirm the association of neurofilament proteins, NSE, vimentin, and tubulin with the mature cells, protein immunoblot analysis (D. W. Speicher, J. S. Morrow, W. J. Knowles, V. J. Marchesi, Proc. Natl. Acad. Sci. U. S. A. 77,5673 (1980) was conducted. Both in control rat brain and HCN-1A cells the neurofilament antibodies recognized the high molecular weight (200 and 168 kD) species of neurofilament protein. Immunoblot for NSE, vimentin, and tubulin similarly showed identity of protein bands in control rat brain and HCN-1A cells, whereas S-100 and MBP were present in rat brian but not in HCN-1A cells.

c. Neurotransmitter Content

The HCN-1A cells stain positively for SST, GABA, glutamate, CCK-8, and VIP, five neurotransmitters that occur in particularly high density in the cerebral cortex, from which the HCN-1A cells are derived. By contrast, the catecholamine marker enzymes are not present in these cells, consistent with the low density of catecholamines in the cerebral cortex. There is some variation in staining intensity for neurotransmitters from cell to cell as in neural crest cells (M. Sieber-Blum, Prog. Clin. Biol. Res. Res. 85, 485 (1982). the existence of five distinct neurotransmitter candidates in various amounts within a single clonal cell line may be indicative of the pluripotentiality of these cells. Two or more neurotransmitters are often expressed by normal cortical neurons, whereas as many as five neurotransmitters in the same neuron have been observed only rarely (T. Hokfelt, O. Johansson, M. Goldstein, Science 225, 1326 (1984).

Expression of neurotransmitters indicates differentiation of CNS neurons. The neurotransmitter content of differentiated HCN-1A cells was analyzed by immunohistochemical examination, using antisera for a variety of neurotransmitters and neurotransmitter-related enzymes (FIG. 4). The cells are stained positively for somatostatin (SST), GABA, glutamate, cholecystokinin-8 (CCK-8), and vasoactive intestinal polypeptide (VIP). In all instances staining was blocked by preincubating the antiserum with the appropriate antigen. No staining of the cells was apparent with antisera to tyrosine hydroxylase, phenylethanolamine-N-methyltransferase (PNMT), dopamine b-hydroxylase (DBH), serotonin, choline acetyltransferase, or nonimmune serum. In the undifferentiated state, staining for VIP, somatostatin, and CCK-8 was lighter; staining for glutamate was restricted to the perniculear region. Therefore differentiation with IBMX, NGF, and dibutyryl cAMP causes biochemical as well as morphological changes.

The only was in which the cells of cell line HCN-2 differ from those of HCN-1A is that their growth can be stimulated by phorbol esters, whereas HCN-1A cell growth is not affected by phorbol esters. The cells of the cell line also divide more rapidly, with a doubling time of 1-2 days, in contrast to the 2-3 days observed for HCN-1A cells. Cells of this cell line have also been deposited at the American Type Culture Collection in Rockville, Md., under the provisions of the Budapest Treaty and have been granted accession no. CRL 10742.

Sources of Cell Lines

Candidates for sources of the cell lines of this invention, inter alia, non-malignant disorders which result in an increased growth abnormality. These disorders are non-malignant (the cells do not metastasize) but result in an increased tendency for the brain cells to divide. These non-malignant growth abnormalities result in immature but non-malignant cells. Included are patients who have a phakomatosis disorder. Such disorder includes, without limitation, unilateral megalencephaly, tuberous sclerosis, neurofibromatosis, encephalotrigeminal (Sturge-Weber syndrome), and cerebroretinal (von Hipple-Lindau disease). Rasmussen's encephalitis is also a candidate source for cells. The cells can be recovered from either adults or juveniles, but since juvenile cells tend to adapt more readily to cell culture, a juvenile source is preferred. The neuronal epithelial tissue should be obtained and cultured very quickly after removal from the patient. Obtaining the tissue within the first hour after removal is recommended although somewhat longer times of six hours or more may also sometimes be satisfactory. Culture can be accomplished using a medium such as minimal essential medium and fetal bovine serum or Dulbecco's modified Eagle's medium with 10% fetal bovine serum and 0.45% glucose. Desirably the medium will contain D-valine or some alternate agent to prevent fibroblast cell growth.

The term "cell line" as used herein refers to human clonal neuronal cells such as are grown in vitro. A "cell line" is substantially free of other human cells.

Screening and Therapy

The cell lines of this invention provide a ready means to characterize the biochemical and electrophysiological properties of central nervous system neurons and to evaluate the effect of chemicals or biologic materials on properties of neurons. The use of a cell line for screening is, of course, well known in the art and is discussed, inter alia, in Current Methods in Cellular Neurobiology, Parker and McKelvy, Weiley - Interscience, New York (1983). Media for use during screening cell cultures are also known and the selection of a particular culture medium and culture conditions are within the skill of the art. For example, chemicals being screened must be solubilized in the culture media. Thus, solubilizing agent which are nontoxic to cells can be included in the media. Dimethylsufloxide (DMSO) is an example of a solubilizing agent that is nontoxic to many cell lines.

Screening preferably is conducted using a series of concentrations of the chemical or biologic material being screened and a control which usually is the vehicle for the chemical or biologic material. The series of concentrations ideally is selected such that at least the lowest concentration produces no effect. Also, the concentrations preferably are selected such that increasing concentrations produce increasing effects.

When using cultured cells a variety of effects can be monitored. Cell death or cessation of cell growth are relatively nonspecific effects. Alterations in cell morphology also can be evaluated. Additionally, the cells' ability to take up, resist uptake of, or respond to various dyes and other chemicals may be a measure of effect. Trypan blue is an example of a known exclusion dye used to assess effects on cells. Further, changes in the amount of neurotransmitters or other endogenous chemicals or proteins produced or released by the cells may be indicative of effect. For example, increases in extracellular lactate dehydrogeanse levels indicate cell injury.

The cell lines of this invention are also attractive candidates for transplants to the brain following trauma, to treat degenerative brain diseases, or to compensate for the removal of a portion of the brain due to surgery or the like. The cell lines are transplantation candidates not only for the brain, but also for other parts of the body to counteract abnormal nerve functions.

Since the cell lines of this invention are neuronal cell lines, they (or their derivatives) can be employed to provide enzymes or other substances to correct deficiencies in the nervous system. For example, sufferers of Parkinson's disease have a dopamine deficiency whereas sufferers of Alzheimers disease have a deficiency of acetylcholine. While the cell lines of the invention do not normally produce either of these chemicals, derivative cell lines can be produced by genetic engineering techniques to introduce an appropriate gene for production of the chemicals. A transfected cell line then can be transplanted to produce the desired chemical in situ. While specific examples of transfected genes are enumerated here, other genes may also be used. In addition, cell lines which remain stable in continuous culture candidate for the production of derivative cell lines having a wide variety of other modifications including increased growth rate, increased nerve receptors, and the like.

We claim:

1. A continuous non-malignant neuronal cell line, the cells of which:
   a) in the undifferentiated form are essentially free of branched processes;
   b) stain positively for neurofilament protein and neurotransmitters;
   c) do not stain positively for glial fibrillary acidic protein; and
   d) in the presence of nerve growth factor differentiate into cells with long branched processes.

2. The substantially pure continuous human neuronal cell line of claim 1 known as HCN 1-A, deposited as ATCC CRL 10442.

3. The substantially pure continuous human neuronal cell line of claim 1 known as HCN-2, deposited as ATCC CRL 10742.

4. In a screening method wherein cells are grown in vitro and a biologically active compound is added to the cells to determine the effect on the cells, the improvement which comprises employing the cell line of claim 1.

5. The method of claim 4 wherein the cell line employed is HCN 1-A.

6. The method of claim 4 wherein the cell line employed is HCN-2.

* * * * *